US009641827B2

(12) United States Patent
Nishigaki et al.

(10) Patent No.: US 9,641,827 B2
(45) Date of Patent: May 2, 2017

(54) CONTROLLER FOR 3D OBSERVATION APPARATUS, 3D OBSERVATION SYSTEM, AND METHOD OF CONTROLLING THE 3D OBSERVATION APPARATUS

(71) Applicant: OLYMPUS CORPORATION, Hachioji-shi, Tokyo (JP)

(72) Inventors: Yasuhiro Nishigaki, Hachioji (JP); Masakazu Mizoguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/227,221

(22) Filed: Aug. 3, 2016

(65) Prior Publication Data

US 2016/0345000 A1 Nov. 24, 2016

Related U.S. Application Data

(63) Continuation of application No. PCT/JP2015/070727, filed on Jul. 21, 2015.

(30) Foreign Application Priority Data

Jul. 28, 2014 (JP) .................................. 2014-153282

(51) Int. Cl.
*H04N 13/02* (2006.01)
*A61B 1/05* (2006.01)
(Continued)

(52) U.S. Cl.
CPC ..... *H04N 13/0296* (2013.01); *A61B 1/00009* (2013.01); *A61B 1/00193* (2013.01);
(Continued)

(58) Field of Classification Search
CPC ............. H04N 13/0296; H04N 13/026; H04N 2013/0096; H04N 13/0051; G02B 23/2415; A61B 1/00009
See application file for complete search history.

(56) References Cited

U.S. PATENT DOCUMENTS 5,689,365 A * 11/1997 Takahashi .......... A61B 1/00179
348/E13.014
8,743,185 B2 * 6/2014 Yamaguchi ........ G02B 27/2285
348/369
(Continued)

FOREIGN PATENT DOCUMENTS

| JP | 2009-134058 A | 6/2009 |
|---|---|---|
| JP | 2013-090035 A | 5/2013 |
| WO | 2013-054891 A1 | 4/2013 |

OTHER PUBLICATIONS

Oct. 13, 2015 International Search Report issued in Patent Application No. PCT/JP2015/070727.
(Continued)

*Primary Examiner* — Dave Czekaj
*Assistant Examiner* — Tsion B Owens
(74) *Attorney, Agent, or Firm* — Oliff PLC

(57) ABSTRACT

A controller for a 3D observation apparatus performing 3D observation based on parallax using a plurality of optical systems includes the following sections. A start time acquisition section obtains a start time when energization of the 3D observation apparatus is started. An interrupted time acquisition section obtains an interrupted time when previous energization of the 3D observation apparatus is interrupted. A non-active time calculation section calculates a non-active time which is a period of time between the interrupted time and the start time. A determination section determines whether or not misalignment correction to correct misalignment of optical axes of the optical systems is necessary based on the non-active time.

12 Claims, 5 Drawing Sheets

(51) Int. Cl.
*H04N 5/232* (2006.01)
*H04N 13/00* (2006.01)
*A61B 1/00* (2006.01)
*H04N 5/225* (2006.01)
*G02B 23/24* (2006.01)

(52) U.S. Cl.
CPC ....... *G02B 23/2415* (2013.01); *H04N 5/2258* (2013.01); *H04N 5/232* (2013.01); *H04N 13/0051* (2013.01); *H04N 13/026* (2013.01); H04N 2005/2255 (2013.01); H04N 2013/0096 (2013.01)

(56) References Cited

U.S. PATENT DOCUMENTS

| | | | | |
|---|---|---|---|---|
| 9,526,405 | B2* | 12/2016 | Noack | A61B 1/00193 |
| 2003/0060679 | A1* | 3/2003 | Murata | A61B 1/00048 |
| | | | | 600/111 |
| 2012/0092472 | A1* | 4/2012 | Higuchi | A61B 1/00009 |
| | | | | 348/65 |
| 2014/0218479 | A1* | 8/2014 | Nishimura | G02B 23/2415 |
| | | | | 348/46 |

OTHER PUBLICATIONS

Feb. 9, 2017 International Preliminary Report on Patentability in International Application No. PCT/US2015/070727.

* cited by examiner

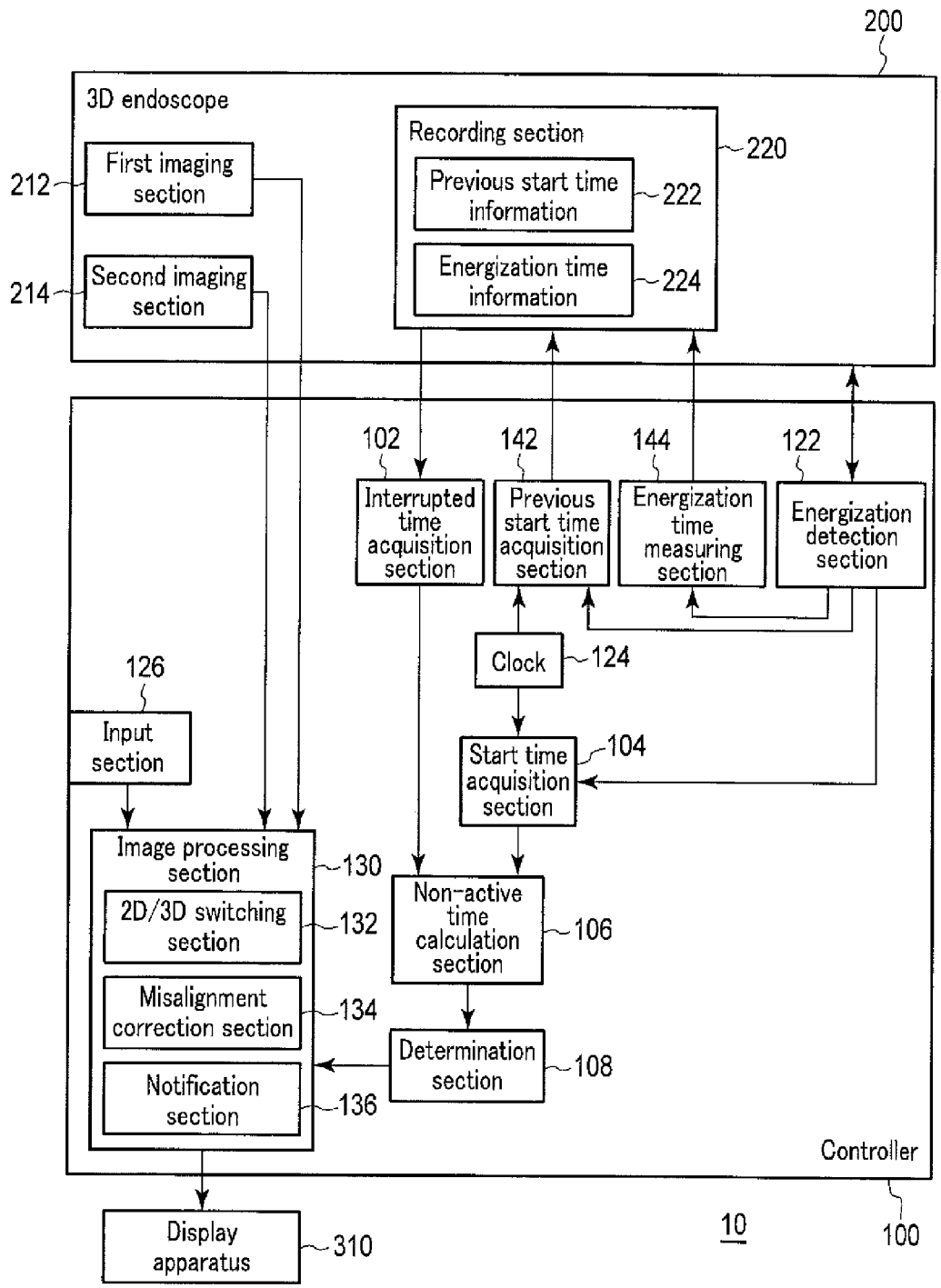
F I G. 1

CONTROLLER FOR 3D OBSERVATION APPARATUS, 3D OBSERVATION SYSTEM, AND METHOD OF CONTROLLING THE 3D OBSERVATION APPARATUS

CROSS-REFERENCE TO RELATED APPLICATIONS

This application is a Continuation Application of PCT Application No. PCT/JP2015/070727, filed Jul. 21, 2015 and based upon and claiming the benefit of priority from prior Japanese Patent Application No. 2014-153282, filed Jul. 28, 2014, the entire contents of all of which are incorporated herein by reference.

BACKGROUND OF THE INVENTION

1. Field of the Invention

The present invention relates to a controller for a 3D observation apparatus, a 3D observation system, and a control method for the 3D observation apparatus.

2. Description of the Related Art

Jpn. Pat. Appln. KOKAI Publication No. 2013-090035, for example, discloses a technology related to a 3D endoscope apparatus for 3D observation based on two images obtained by two optical systems and the parallax of the images. Jpn. Pat. Appln. KCKAI Publication No. 2013-090035 discloses that a misalignment occurs in an optical system of a 3D endoscope when the 3D endoscope is treated in an autoclave. Unless a correction is made to the misalignment, a 3D image cannot be properly constructed. Jpn. Pat. Appln. KOKAI Publication No. 2013-090035 discloses a misalignment correction which is achieved by adjusting an image for the right-eye to an image for the left-eye by a translation process. However, performing an alignment correction when it is unnecessary is troublesome.

BRIEF SUMMARY OF THE INVENTION

According to an aspect of the invention, a controller for a 3D observation apparatus performing 3D observation based on parallax using a plurality of optical systems includes a start time acquisition section which obtains a start time when energization of the 3D observation apparatus is started; an interrupted time acquisition section which obtains an interrupted time when previous energization of the 3D observation apparatus is interrupted; a non-active time calculation section which calculates a non-active time which is a period of time between the interrupted time and the start time; and a determination section which determines whether or not misalignment correction to correct misalignment of optical axes of the optical systems is necessary based on the non-active time.

According to an aspect of the invention, a 3D observation system includes a 3D observation apparatus performing 3D observation based on parallax using a plurality of optical systems; a start time acquisition section which obtains a start time when energization of the 3D observation apparatus is started; an interrupted time acquisition section which obtains an interrupted time when previous energization of the 3D observation apparatus is interrupted; a non-active time calculation section which calculates a non-active time which is a period of time between the interrupted time and the start time; a determination section which determines whether or not misalignment correction to correct misalignment of optical axes of the optical systems is necessary based on the non-active time; and an image processing section which constructs a 3D image based on a plurality of images obtained using the plurality of optical systems, and which performs the misalignment correction by changing positional relationships of a plurality of images when the misalignment correction is necessary.

According to an aspect of the invention, a method of controlling a 3D observation apparatus performing 3D observation based on parallax using a plurality of optical systems includes acquiring a start time when energization of the 3D observation apparatus is started; acquiring an interrupted time when previous energization of the 3D observation apparatus is interrupted; calculating a non-active time which is a period of time between the interrupted time and the start time; and determining whether or not misalignment correction to correct influence of misalignment of optical axes of the optical systems is necessary based on the non-active time.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing an outline of a configuration example of an endoscope system according to a first embodiment of the present invention;

DETAILED DESCRIPTION OF THE INVENTION

First Embodiment

Figure 2:
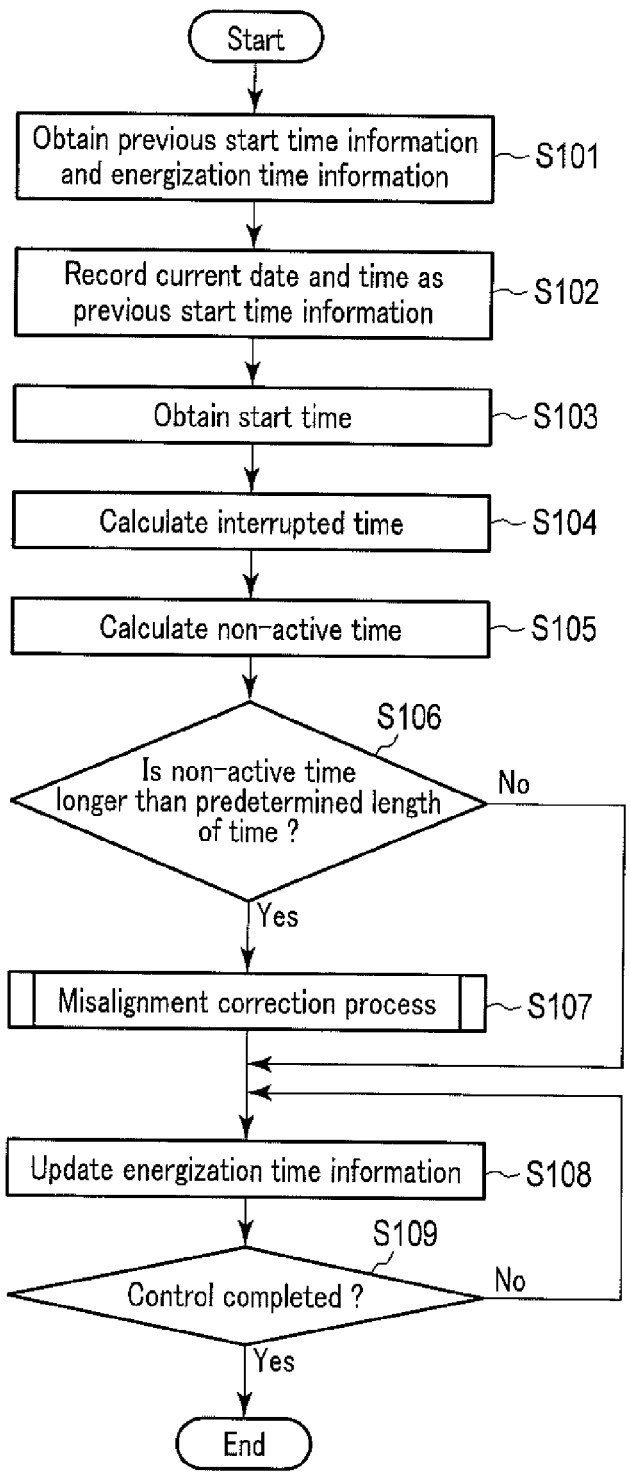
FIG. 2 is a flowchart showing an example of processing according to the first embodiment.

The first embodiment of the present invention will be described with reference to the drawings. An endoscope system 10 will be described as an example of the embodiments of a 3D observation system according to the present invention. FIG. 1 illustrates an outline of a configuration example of the endoscope system 10 according to the present embodiment. The endoscope system 10 comprises a 3D endoscope 200, a controller 100, and a display apparatus 310.

The 3D endoscope 200 is an endoscope having a function for a 3D observation apparatus which obtains a 3D image using parallax. For this reason, the 3D endoscope 200 has two imaging sections, i.e., a first imaging section 212 and a second imaging section 214. Each of the first imaging section 212 and the second imaging section 214 has an optical system (not shown such as a lens, etc.) and an imaging element. Each of the first imaging section 212 and the second imaging section 214 generates an image signal.

The endoscope system 10 constructs a 3D image based on an image obtained by the first imaging section 212 and an image obtained by the second imaging section 214, and presents the 3D image to a user. To construct a 3D image properly, it is necessary to correctly adjust a parallax of the image obtained by the first imaging section 212 and the image obtained by the second imaging section 214. For example, when the 3D endoscope 200 is treated in an autoclave to perform sterilization during a process of cleaning the 3D endoscope 200, a misalignment occurs between an optical axis of the first imaging section 212 and an optical axis of the second imaging section 214, and sometimes the 3D image cannot be properly constructed. In such a case, it is necessary to perform a correction to move the image obtained by the first imaging section 212 and the image obtained by the second imaging section 214 by a misaligned amount of the optical axis, for example. Hereinafter, such a process of correcting a misalignment in optical axes will be referred to as a misalignment correction. The endoscope system 10 according to the present embodiment performs the misalignment correction only when necessary, for example, when cleaning is performed, and does not perform the unnecessary misalignment correction.

The 3D endoscope 200 is supplied with power from the controller 100. In the present embodiment, a history of the controller 100 supplying power to the 3D endoscope 200, i.e., energization of the 3D endoscope 200, is recorded. The 3D endoscope 200 has a recording section 220. The recording section 220 stores previous start time information 222 and energization time information 224. The previous start time information 222 includes information of a start date and time of power supply from the controller 100 to the 3D endoscope 200, i.e., previous energization of the 3D endoscope 200 which has already been stopped. The energization time information 224 includes a time during which previous energization, which has already been stopped, was performed, i.e., a period of time during which the controller 100 supplies power to the 3D endoscope 200.

A display apparatus 310 is a 3D monitor. A user can perform 3D-image observation by looking at the 3D monitor through a pair of 3D glasses. The display apparatus 310 is not limited to an apparatus used with a pair of 3D glasses; it may be any apparatus as long as it is capable of 3D display.

The controller 100 is for controlling the operation of the 3D endoscope 200. The controller 100 may be realized by, for example, a computer. In other words, each section included in the controller 100 may be realized by a computer including an element such as a central processing unit (CPU) or an application specific integrated circuit (ASIC), for example.

The controller 100 comprises an interrupted time acquisition section 102, a start time acquisition section 104, a non-active time calculation section 106, a determination section 108, an energization detection section 122, a clock 124, an input section 126, an image processing section 130, a previous start time acquisition section 142, and an energization time measuring section 144.

The energization detection section 122 detects whether or not the controller 100 supplies power to the 3D endoscope 200, i.e., whether or not there is energization of the 3D endoscope 200. The clock 124 is a clock for outputting a current date and time. The input section 126 includes a common input apparatus, such as a switch, dial, and a keyboard, etc. The input section 126 obtains an instruction from a user. The input section 126 outputs the obtained instruction to the image processing section 130.

The interrupted time acquisition section 102 reads the previous start time information 222 and the energization time information 224 recorded in the recording section 220 provided in the 3D endoscope 200. The interrupted time acquisition section 102 obtains the date and time when the previous energization was stopped as an interrupted time, based on the previous start time information 222 and the energization time information 224.

The start time acquisition section 104 obtains information regarding a start of energization from the energization detection section 122, and the date and time of the energization start from the clock 124. The start time acquisition section 104 thus obtains the date and time when energization of the 3D endoscope 200 starts as a start time.

The non-active time calculation section 106 obtains the interrupted time from the interrupted time acquisition section 102, and obtains the start time from the start time acquisition section 104. The non-active time calculation section 106 calculates the time between the interrupted time and the start time, i.e., the time during when energization of the 3D endoscope 200 was not performed, as a non-active time.

The determination section 108 obtains the non-active time from the non-active time calculation section 106. The determination section 108 determines whether or not the misalignment correction is necessary based on the non-active time. If misalignment correction is necessary, the determination section 108 notifies the image processing section 130 of the necessity.

The image processing section 130 obtains image signals from the first imaging section 212 and the second imaging section 214, and performs image processing on the obtained image signals. This image processing includes constructing a 3D image based on the image data obtained by the first imaging section 212 and the image data obtained by the second imaging section 214. The image processing section 130 outputs to the display apparatus 310 the image signal after the image processing, and displays the 3D image on the display apparatus 310.

The image processing section 130 has a 2D/3D switching section 132. The 2D/3D switching section 132 causes the image processing section 130 to stop constructing the 3D image when misalignment correction is necessary. At this time, the 2D/3D switching section 132 causes the image processing section 130 to create a 2D image based on an image obtained by the first imaging section 212 or the second imaging section 214. The image processing section 130 creates the 2D image, and displays the created 2D image on the display apparatus 310. The 20/3D switching section 132 causes the image processing section 130 to construct a 3D image again when misalignment correction is completed. As a result, the image processing section 130 constructs a 3D image, and displays the constructed 3D image on the display apparatus 310.

The image processing section 130 has a misalignment correction section 134. In order to correct the misalignment between the optical axes of the first imaging section 212 and the second imaging section 214, the misalignment correction section 134 performs misalignment correction to change the positional relationship between the image obtained by the first imaging section 212 and the image obtained by the second imaging section 214 for the amount of misalignment in the optical axes.

The image processing section 130 has a notification section 136. When misalignment correction is necessary, the notification section 136 performs a process of notifying a user about a necessity of misalignment correction. For example, the notification section 136 includes an indication of the necessity of misalignment correction in an image to be displayed on the display apparatus 310. By this indication, the user is informed that misalignment correction is necessary.

The previous start time acquisition section 142 obtains information regarding a start of energization from the energization detection section 122, and the date and time of the energization start from the clock 124. The previous start time acquisition section 142 records the date and time when energization starts in the recording section 220 of the 3D endoscope 200 as previous start time information 222.

The energization time measuring section 144 obtains information of the energization status from the energization detection section 122, and records in the recording section 220 a time during which the energization continues as energization time information 224. The energization time information 224 is periodically updated. Accordingly, a period during which current energization continues is constantly recorded as the energization time information 224 in the recording section 220.

The operation related to misalignment correction by the controller according to the present embodiment is described with reference to the flowchart shown in FIG. 2. The process described herein is performed when the 3D endoscope 200 is connected to the controller 100 and the energization detection section 122 detects that energization of the 3D endoscope 200 has started, for example.

In step S101, the interrupted time acquisition section 102 of the controller 100 reads the previous start time information 222 and the energization time information 224 from the recording section 220 of the 3D endoscope 200.

In step S102, the previous start time acquisition section 142 of the controller 100 obtains a current date and time from the clock 124, and records the current data and time in the recording section 220 as the previous start time information 222.

In step S103, the start time acquisition section 104 of the controller 100 obtains a current date and time from the clock 124, and outputs the current date and time to the non-active time calculation section 106 as the start time. In step S104, the interrupted time acquisition section 102 of the controller 100 calculates an interrupted time based on the previous start time information 222 and the energization time information 224. In other words, the interrupted time acquisition section 102 calculates a date and time obtained by adding an energization time, which is a period during which energization is performed, to the start date and time of previous energization, as an interrupted time. The interrupted time acquisition section 102 outputs the interrupted time to the non-active time calculation section 106.

In step S105, the non-active time calculation section 106 of the controller 100 obtains the interrupted time and the start time. The non-active time calculation section 106 calculates the difference between the interrupted time and the start time as a non-active time. The non-active time indicates a period of time when the 3D endoscope 200 is not energized. The non-active time calculation section 106 outputs the calculated non-active time to the determination section 108.

In step S106, the determination section 108 of the controller 100 determines whether or not the non-active time is longer than a predetermined length of time. Herein, the predetermined length of time is set at a length of time required for cleaning the 3D endoscope 200, for example. The predetermined length of time is, for example, one hour. When the non-active time is longer than the predetermined length of time, the cleaning of the 3D endoscope 200 may be performed, and there is a possibility that the optical axes of the first imaging section 212 and the second imaging section 214 are misaligned. If it is determined that the non-active time is longer than the predetermined length of time, the process proceeds to step S107.

In step S107, the image processing section 130 of the controller 100 performs misalignment correction process. The misalignment correction process includes misalignment correction. The details of the misalignment correction process will be described later. After the misalignment correction process, the process proceeds to step S108.

If it is determined in step S106 that the non-active time is not longer than the predetermined length of time, it is a case where misalignment correction is unnecessary. If it is determined that the non-active time is not longer than the predetermined length of time, the process proceeds to step S108.

In step S108, the energization time measuring section 144 of the controller 100 updates the energization time information 224 recorded in the recording section 220. The energization time measuring section 144 counts up, for example, and records the value in the recording section 220 as the energization time information 224.

In step S109, the controller 100 determines whether or not the control is completed. When the user finishes using the endoscope system 10 and inputs the finishing in the controller 100, for example, the control is completed. When the 3D endoscope 200 is removed from the controller 100 and the energization is canceled, the control is finished. If it is determined that the control is not finished, the process returns to step S108. Thus, the energization time measuring section 144 continues counting up until the control is completed, and the energization time information recorded in the recording section 220 is successively updated. Meanwhile, the 3D endoscope 200 is used by the user for 3D observation. On the other hand, if it is determined in step S109 that the control is completed, the process is finished.

Next, the misalignment correction process performed in step S107 is described with reference to the flowchart of FIG. 3.

In step S201, the notification section 136 of the image processing section 130 performs a process to inform the user that misalignment correction is necessary. For example, the notification section 136 causes the display apparatus 310 to display an indication that misalignment correction is necessary. The notification process may be performed using other means, such as sound.

In step S202, the 2D/3D switching section 132 of the image processing section 130 causes the image processing section 130 to create and display a 2D image. At this time, the image processing section 130 creates a 2D image based on one of the image obtained by the first imaging section 212 and the image obtained by the second imaging section 214. The image processing section 130 causes the display apparatus 310 to display the created 2D image.

If the misalignment correction is performed by moving either one of the image obtained by the first imaging section 212 and the image obtained by the second imaging section 214, it is preferable to create a 2D image based on the image which is not moved and serves as a reference. Continuity with the display of later 3D image can be maintained by using a reference image.

In step S203, the image processing section 130 causes the display apparatus 310 to display an indication to ask the user whether or not misalignment correction is performed.

In step S204, the image processing section 130 determines whether or not an input indicating that misalignment correction is to be performed has been made. If it is determined that the input has not been made, the process repeats step S204. In other words, the process waits for such an input. On the other hand, when such an input has been made, the process proceeds to step S205.

In step S205, the misalignment correction section 134 of the image processing section 130 performs misalignment correction. For example, during misalignment correction, an adjustment is made by moving the image obtained by the second imaging section 214 in accordance with a change of its optical axis, using the image obtained by the first imaging section 212 as a reference. At this time, the optical system of the first imaging section 212 becomes a reference optical system. When misalignment correction is completed, the process proceeds to step S206.

In step S206, the notification section 136 of the image processing section 130 performs a process to notify the user that misalignment correction is completed.

In step S207, the 2D/3D switching section 132 of the image processing section 130 causes the image processing section 130 to perform construction and display of a 3D image. At this time, the image processing section 130 constructs a 3D image based on the image obtained by the first imaging section 212 and the image obtained by the second imaging section 214. The image processing section 130 causes the display apparatus 310 to display the constructed 3D image. Hereinafter, a 3D image is displayed on the display apparatus 310. The alignment correction process is completed, and the process returns to step S107.

According to the present embodiment, whether or not the cleaning of the 3D endoscope 200, which requires misalignment correction, has been performed is determined based on a non-active time. In other words, when a non-active time, which is a period of time during which energization is not performed, is shorter than a predetermined length of time, it is determined that the cleaning has not been performed; if longer, it is determined that the cleaning has been performed. By such a determination, it is possible to prompt the user to perform misalignment correction only when necessary. Thus, stress to a user due to unnecessary misalignment correction can be reduced. It is also possible to prevent displaying improperly-constructed 3D image on the display apparatus 310, because a 2D display is created when misalignment correction is necessary.

It should be noted that the controller 100 can correctly calculate the non-active time in the present embodiment, regardless a type of 3D endoscope 200 connected to the controller 100, because information related to the interrupted time during when previous energization is interrupted is recorded in the recording section 220, which is provided in the 3D endoscope 200. In the recording section 220, the previous start time information 222 which is recorded when energization is started, and the energization time information 224 indicating a time length for the energization which is subsequently updated at the time of energization are recorded as information for calculating an interrupted time. Thus, the information for calculating an interrupted time can be maintained in the recording section 220 even when energization is abruptly interrupted during energization of the 3D endoscope 200. Thus, the interrupted time acquisition section 102 can correctly calculate an interrupted time even when energization of the 3D endoscope is abruptly interrupted.

In the above-described embodiment, a case where an image obtained by the second imaging section 214 is moved using an image obtained by the first imaging section 212 as a reference is described as an example of a misalignment correction method. However, a misalignment correction method is not limited thereto. For example, a predetermined reference position may be set, an image obtained by the first imaging section 212 may be adjusted to the predetermined reference position, and an image obtained by the second imaging section 214 may be adjusted to a reference position corresponding to the predetermined reference position. The reference position herein is related to a reference position of the optical axis of the optical system of the first imaging section 212 and a reference position of the optical axis of the optical system of the second imaging section 214 in a case where a 3D image is properly constructed, for example. In other words, the position of the image obtained by the first imaging section 212 is adjusted in accordance with the misalignment from the reference position of the optical axis of the optical system of the first imaging section 212. Similarly, the position of the image obtained by the second imaging section 214 is adjusted in accordance with the misalignment from the reference position of the optical axis of the optical system of the second imaging section 214. In this case, the creation of 2D image is discretionarily based on either one of the image obtained by the first imaging section 212 and the image obtained by the second imaging section 214. The above predetermined reference position may be set at a middle point of a line segment connecting the reference position of the image obtained by the first imaging section 212 (e.g., a central coordinate of the image obtained by the first imaging section 212), and the reference position of the image obtained by the second imaging section 214 (e.g., a central coordinate of the image obtained by the second imaging section 214).

The misalignment correction may be performed not only by image processing, but also by adjusting the optical systems of the first imaging section 212 and the second imaging section 214, for example.

Figure 3:
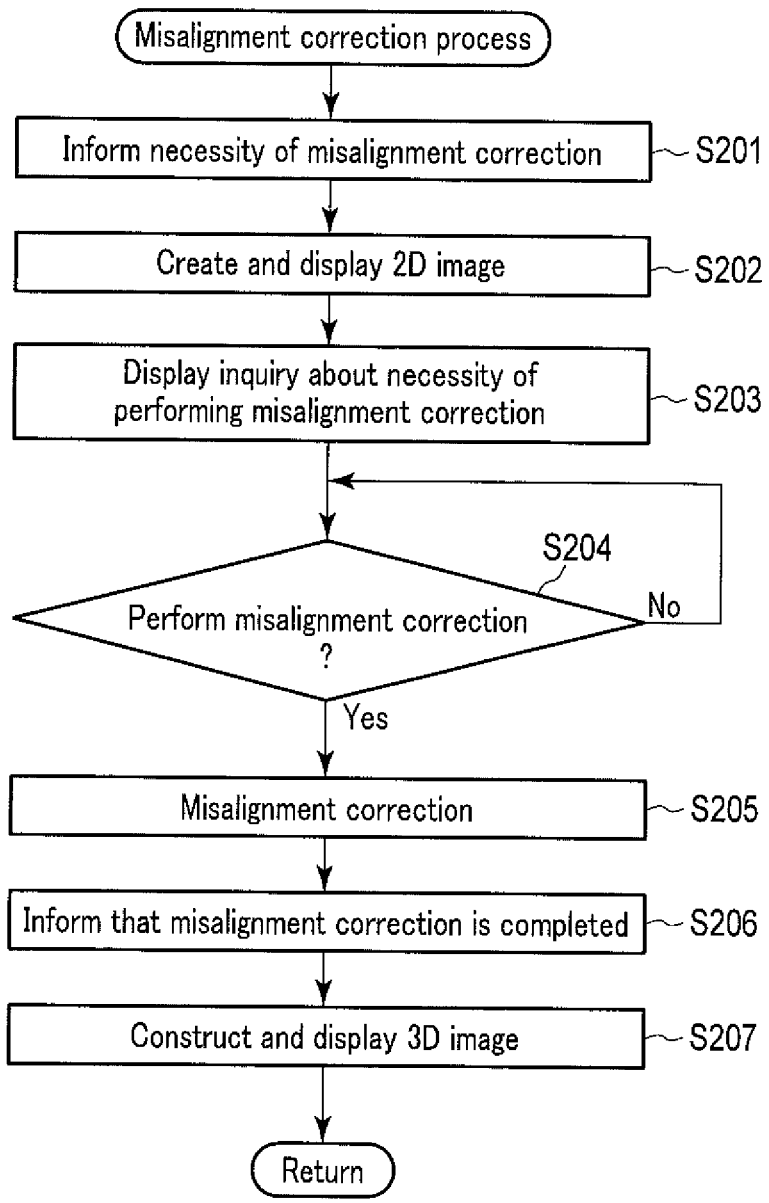
FIG. 3 is a flowchart showing an example of a misalignment correction process according to the first embodiment.

The order of the process described with reference to FIGS. 2 and 3 is changeable as appropriate, and the process may be partially omitted. For example, the order of the process performed between step S101 and step S103 is discretionary. The process may be configured to perform misalignment correction immediately when necessary, without waiting for a user's instruction to perform misalignment correction in step S204.

In the present embodiment, the case where a 3D endoscope is used as a 3D observation apparatus is described; however, the technology described herein may be applied to various 3D observation apparatuses that require misalignment correction when a time during which no energization is performed is long.

Modification of First Embodiment

Next, a modification of the first embodiment will be described. Herein, differences between the present modification and the first embodiment will be described, and elements specified by the same reference numbers carry out the same operations, and a duplicate description of such elements will be omitted.

Figure 4:
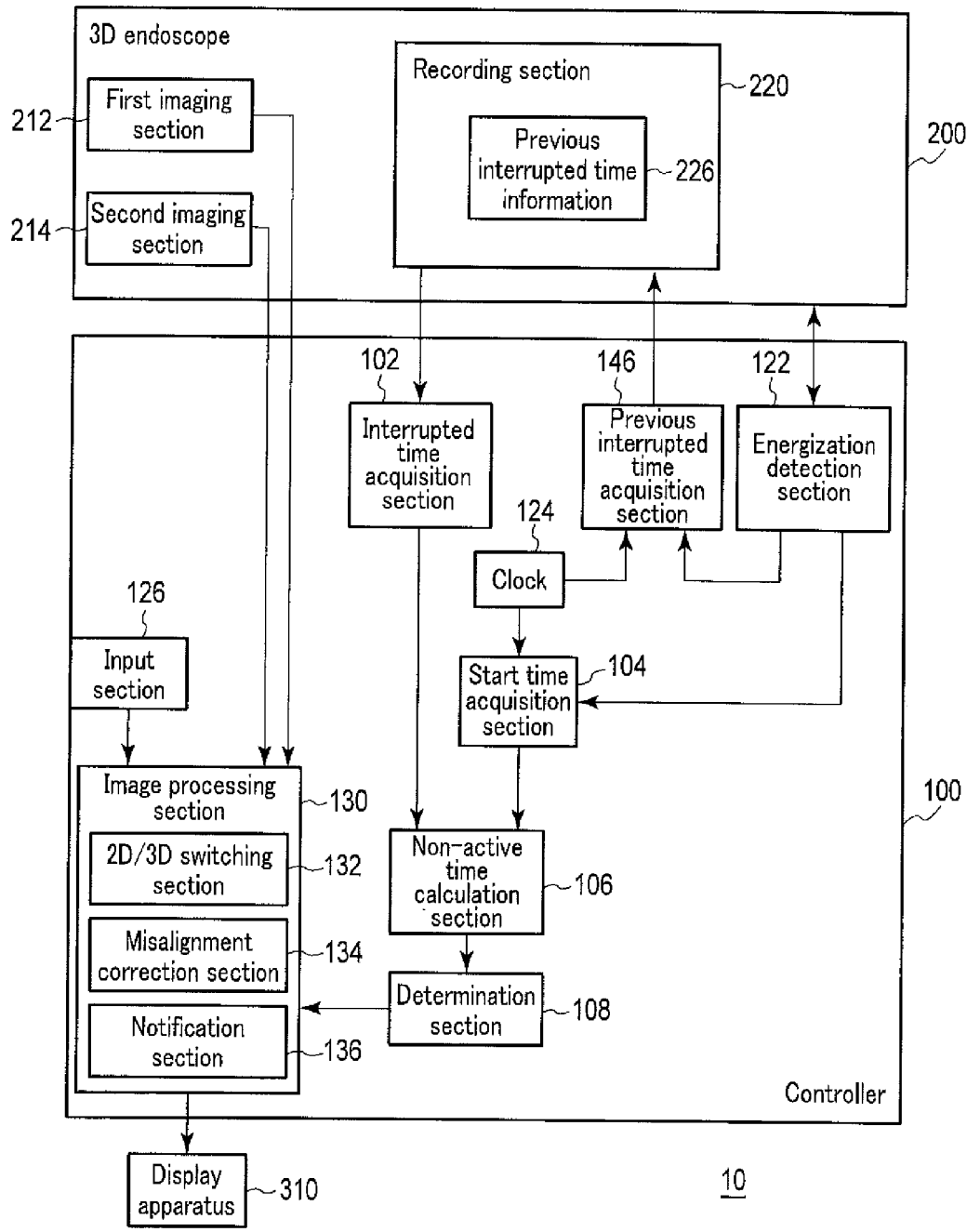
FIG. 4 is a block diagram showing an outline of a configuration example of an endoscope system according to a modification of the first embodiment.

FIG. 4 illustrates the outline of an example of the configuration of the endoscope system 10 according to the present modification. In the first embodiment, the energization time information 224 is recorded in the recording section 220 of the 3D endoscope 200; however, in the present modification, previous interrupted time information 226 is recorded in the recording section 220. The previous interrupted time information 226 includes information of a date and time when a previous energization was interrupted. Instead of the previous start time acquisition section 142 and the energization time measuring section 144, a previous interrupted time acquisition section 146 is provided in the controller 100.

The previous interrupted time acquisition section 146 records a date and time obtained from the clock 124 in the recording section 220 as previous interrupted time information, immediately before energization of the 3D endoscope 200 is interrupted. When information that energization is started is obtained from the energization detection section 122, the interrupted time acquisition section 102 obtains the previous interrupted time information recorded in the recording section 220 as an interrupted time.

Similarly to the first embodiment, when information that energization is started is obtained from the energization detection section 122, the start time acquisition section 104 obtains from the clock 124 the date and time of acquisition the information as a start time. The non-active time calculation section 106 calculates a non-active time based on the interrupted time and start time obtained as described above. The determination section 108 determines whether or not misalignment correction is necessary based on the calculated non-active time. If it is determined that misalignment correction is necessary, the image processing section 130 performs the misalignment correction process similar to the first embodiment.

According to the present modification, an advantageous effect of performing misalignment correction only when necessary can be achieved, similarly to the first embodiment. Furthermore, according to the present modification, in comparison to the first embodiment, the process performed at the controller 100 can be reduced, and an amount of communication between the controller 100 and the 3D endoscope 200 can also be reduced.

Second Embodiment

The second embodiment of the present invention is described. Herein, differences between the second embodiment and the modification of the first embodiment are described, and elements specified by the same reference numbers carry out the same operations, and a duplicate description of such elements will be omitted.

Figure 5:
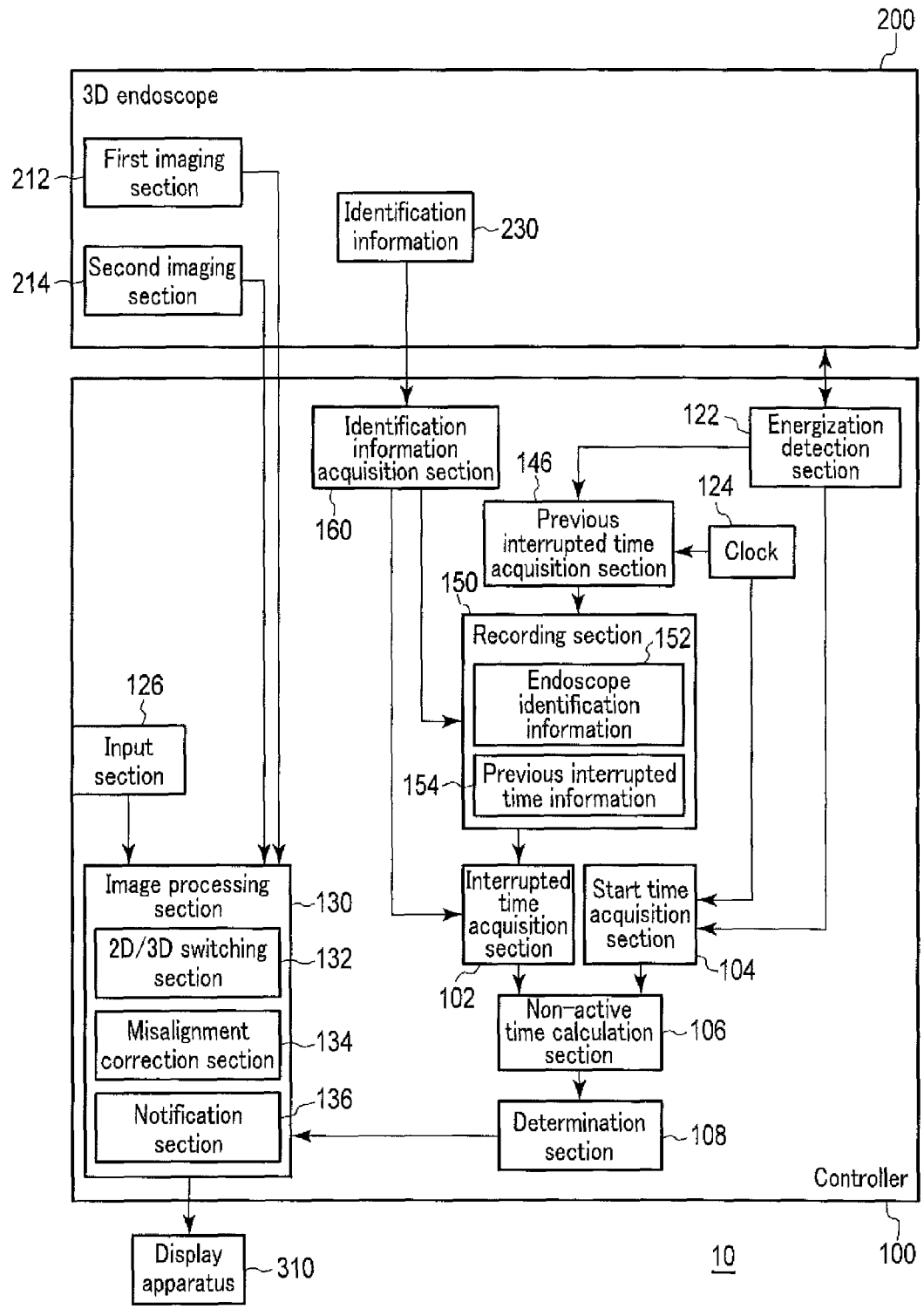
FIG. 5 is a block diagram showing an outline of a configuration example of an endoscope system according to a second embodiment.

FIG. 5 illustrates the outline of the configuration example of the endoscope system 10 according to the present embodiment. In the present embodiment, the recording section, which is provided in the 3D endoscope 200 in the modification of the first embodiment, is provided in the controller 100. Endoscope identification information 152 and previous interrupted time information 154 are recorded in the recording section 150 provided in the controller 100

The previous interrupted time acquisition section 146 obtains from the energization detection section 122 information that energization of the 3D endoscope 200 is interrupted, and obtains a date and time of acquisition of the information from the clock 124. The previous interrupted time acquisition section 146 records a time when energization is interrupted as previous interrupted time information 154 based on the information.

Identification information 230, which is unique to each 3D endoscope 200, is recorded in the 3D endoscope 200 according to the present embodiment. An identification information acquisition section 160 for reading the identification information 230 is provided in the controller 100. The identification information acquisition section 160 records the read information in the recording section 150 as endoscope identification information 152. The endoscope identification information 152 and the previous interrupted time information 154 are related to each other. In other words, the previous interrupted time information 154 is recorded for each endoscope identification information 152.

The interrupted time acquisition section 102 according to the present embodiment obtains identification information from the identification information acquisition section 160, and obtains the previous interrupted time information 154 corresponding to the identification information from the recording section 150 as an interrupted time.

Similarly to the modification of the first embodiment, the start time acquisition section 104 obtains from the clock 124 the date and time when the energization starts. The non-active time calculation section 106 calculates a non-active time based on the interrupted time and start time obtained as described above. The determination section 108 determines whether or not misalignment correction is necessary based on the calculated non-active time. If it is determined that misalignment correction is necessary, the image processing section 130 performs the misalignment correction process similar to the first embodiment.

According to the present embodiment, similarly to the first embodiment, an advantageous effect of performing the misalignment correction process only when necessary can be achieved. Furthermore, according to the present embodiment, in comparison to the first embodiment and the modification of the first embodiment, an amount of communication between the controller 100 and the 3D endoscope 200 can be reduced. Since the endoscope identification information 152 and the previous interrupted time information 154 are related to each other and recorded in the recording section 150, the controller 100 can correctly calculate the non-active time in the present embodiment, regardless a type of 3D endoscope 200 connected to the controller 100. According to the present embodiment, similarly to the first embodiment, an interrupted time is recorded in the recording section 150 even when energization is abruptly interrupted during energization of the 3D endoscope 200.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A controller for a 3D observation apparatus performing 3D observation based on parallax using a plurality of optical systems, the controller comprising:
   a start time acquisition section which obtains a start time when energization of the 3D observation apparatus is started;
   an interrupted time acquisition section which obtains an interrupted time when previous energization of the 3D observation apparatus is interrupted;
   a non-active time calculation section which calculates a non-active time which is a period of time between the interrupted time and the start time; and a determination section which determines whether or not misalignment correction to correct misalignment of optical axes of the optical systems is necessary based on the non-active time.

2. The controller according to claim 1, further comprising:
a previous start time acquisition section which records a previous start time when the previous energization was started in a recording section; and
an energization time measuring section which measures an energization time which is a time elapsed since the previous start time and indicates a time during which energization is performed, and which records the energization time in the recording section;
wherein the interrupted time acquisition section determines the interrupted time based on the previous start time and the energization time.

3. The controller according to claim 2, wherein the recording section is provided in the 3D observation apparatus.

4. The controller according to claim 1, further comprising a 2D/3D switching section which prompts performing 2D observation using any one of the plurality of optical systems when the misalignment correction is necessary but has not been performed, and prompts 3D observation after the misalignment correction is completed.

5. The controller according to claim 4, wherein
one of the plurality of optical systems is defined as a reference optical system, and the misalignment correction is correction to change a position of an image obtained using other optical systems of the plurality of optical systems in accordance with an image obtained using the reference optical system, and
the 2D observation is performed using the reference optical system.

6. The controller according to claim 4, wherein
reference positions are provided respectively for images obtained using each of the plurality of optical systems, and the misalignment correction is a correction to change the positions of the images to the reference positions, and
the 2D observation is performed using any one of the plurality of optical systems.

7. The controller according to claim 1, wherein
a recording section in which the interrupted time is recorded is provided in the 3D observation apparatus, and
the interrupted time acquisition section obtains the interrupted time from the recording section.

8. The controller according to claim 1, wherein
the 3D observation apparatus has identification information unique to each 3D apparatus, and
the controller further comprises a recording section which records a combination of the identification information and the interrupted time.

9. The controller according to claim 1, further comprising a notification section which notifies a necessity of the misalignment correction when it is determined that the misalignment correction is necessary.

10. The controller according to claim 1, further comprising a misalignment correction section which performs the misalignment correction by changing a positional relationship among a plurality of images obtained using the plurality of optical systems.

11. A 3D observation system comprising:
a 3D observation apparatus performing 3D observation based on parallax using a plurality of optical systems;
a start time acquisition section which obtains a start time when energization of the 3D observation apparatus is started;
an interrupted time acquisition section which obtains an interrupted time when previous energization of the 3D observation apparatus is interrupted;
a non-active time calculation section which calculates a non-active time which is a period of time between the interrupted time and the start time;
a determination section which determines whether or not misalignment correction to correct misalignment of optical axes of the optical systems is necessary based on the non-active time; and
an image processing section which constructs a 3D image based on a plurality of images obtained using the plurality of optical systems, and which performs the misalignment correction by changing positional relationships of a plurality of images when the misalignment correction is necessary.

12. A method of controlling a 3D observation apparatus performing 3D observation based on parallax using a plurality of optical systems, the method comprising:
acquiring a start time when energization of the 3D observation apparatus is started;
acquiring an interrupted time when previous energization of the 3D observation apparatus is interrupted;
calculating a non-active time which is a period of time between the interrupted time and the start time; and
determining whether or not misalignment correction to correct influence of misalignment of optical axes of the optical systems is necessary based on the non-active time.

* * * * *